(12) United States Patent  (10) Patent No.: US 7,490,636 B2
Bartholomew  (45) Date of Patent: Feb. 17, 2009

(54) BY-PASS LINE CONNECTOR FOR COMPOUNDING SYSTEM

(75) Inventor: Joel Bartholomew, Danielsville, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 124 days.

(21) Appl. No.: 11/713,268

(22) Filed: Mar. 2, 2007

(65) Prior Publication Data

US 2007/0151618 A1 Jul. 5, 2007

Related U.S. Application Data

(62) Division of application No. 10/942,529, filed on Sep. 16, 2004, now Pat. No. 7,204,277.

(51) Int. Cl.
B65B 1/04 (2006.01)
B01D 29/00 (2006.01)

(52) U.S. Cl. .................... 141/10; 141/99; 141/105; 141/114; 141/236; 210/254

(58) Field of Classification Search .......... 141/2, 141/10, 99, 100, 103, 105, 114, 234, 236; 210/252–254, 257.1, 258; 604/80
See application file for complete search history.

(56) References Cited

U.S. PATENT DOCUMENTS

| 3,941,126 | A | 3/1976 | Dietrich et al. |
| 4,467,844 | A | 8/1984 | DiGianfilippo et al. |
| 4,513,796 | A | 4/1985 | Miller et al. |
| 4,648,430 | A | 3/1987 | DiGianfilippo et al. |
| 4,653,010 | A | 3/1987 | Figler et al. |
| 4,712,590 | A | 12/1987 | Gianfilippo |
| 4,718,467 | A | 1/1988 | DiGianfilippo et al. |
| 4,789,014 | A | 12/1988 | DiGianfilippo et al. |
| 4,823,833 | A | 4/1989 | Hogan et al. |
| 4,922,975 | A | 5/1990 | Polaschegg |
| 4,967,811 | A | 11/1990 | DiGianfilippo et al. |
| 5,025,954 | A | 6/1991 | Dunnous |
| 5,040,699 | A | 8/1991 | Gangemi |
| 5,056,568 | A | 10/1991 | DiGianfilippo et al. |
| 5,076,332 | A | 12/1991 | Lewis et al. |
| 5,085,256 | A | 2/1992 | Kircher et al. |
| 5,128,048 | A | 7/1992 | Stewart et al. |
| 5,180,504 | A | 1/1993 | Johnson et al. |
| 5,313,992 | A | 5/1994 | Grabenkort |
| 5,316,181 | A | 5/1994 | Burch |
| 5,364,526 | A | 11/1994 | Matkovich et al. |
| 5,402,834 | A | 4/1995 | Levin et al. |

(Continued)

FOREIGN PATENT DOCUMENTS

WO WO 00/09069 2/2000

(Continued)

Primary Examiner—Timothy L Maust
(74) Attorney, Agent, or Firm—RatnerPrestia

(57) ABSTRACT

A method for selectively dispensing fluid components through a bypass, the bypass having a fluid passage with an inlet, a first outlet that is unsealed, and a second outlet that is sealed, includes the steps of inserting a tubing line into the second outlet to unseal the second outlet, sealing the first outlet to prevent flow of fluid through the first outlet, and delivering a first fluid component into the inlet of the bypass and through the second outlet.

16 Claims, 3 Drawing Sheets

U.S. PATENT DOCUMENTS

| | | |
|---|---|---|
| 5,431,185 A | 7/1995 | Shannon et al. |
| 5,431,201 A | 7/1995 | Torchia et al. |
| 5,431,202 A | 7/1995 | Dikeman et al. |
| 5,450,847 A | 9/1995 | Kampfe et al. |
| 5,464,047 A | 11/1995 | Muscara |
| 5,470,488 A | 11/1995 | Matkovich et al. |
| 5,507,412 A | 4/1996 | Ebert et al. |
| 5,510,621 A | 4/1996 | Goldman |
| 5,511,594 A | 4/1996 | Brennan et al. |
| 5,592,940 A | 1/1997 | Kampfe et al. |
| 5,597,094 A | 1/1997 | Vilbert |
| 5,601,730 A | 2/1997 | Page et al. |
| 5,626,172 A | 5/1997 | Schumacher et al. |
| 5,637,103 A | 6/1997 | Kerwin et al. |
| 5,697,407 A | 12/1997 | Lasonde |
| 5,750,998 A | 5/1998 | Goldman |
| 5,772,966 A | 6/1998 | Maracas et al. |
| 5,820,048 A | 10/1998 | Shereyk et al. |
| 5,927,349 A | 7/1999 | Martucci et al. |
| 5,989,423 A | 11/1999 | Karmen et al. |
| 6,079,462 A | 6/2000 | Martucci et al. |
| 6,199,603 B1 | 3/2001 | DiGianfilippo et al. |
| 6,202,711 B1 | 3/2001 | Martucci et al. |
| 6,213,174 B1 | 4/2001 | Cook et al. |
| 6,296,450 B1 | 10/2001 | Westberg et al. |
| 6,319,243 B1 | 11/2001 | Becker et al. |
| 6,488,860 B2 | 12/2002 | Mari et al. |
| 6,669,681 B2 | 12/2003 | Jepson et al. |
| 2002/0035412 A1 | 3/2002 | Kircher et al. |

FOREIGN PATENT DOCUMENTS

| | | |
|---|---|---|
| WO | WO 03/058507 A1 | 7/2003 |
| WO | WO 2005/061328 | 7/2005 |
| WO | 2005/012169 | 11/2006 |

…

BY-PASS LINE CONNECTOR FOR COMPOUNDING SYSTEM

RELATED APPLICATION

This divisional application is being filed in accordance with 35 U.S.C. §121 and claims priority to U.S. patent application Ser. No. 10/942,529, filed Sep. 16, 2004 now U.S. Pat. No. 7,204,277, the entire contents of which is incorporated by reference herein.

FIELD OF THE INVENTION

The present invention relates generally to compounder systems, and more particularly, to a compounder system having a bypass for transferring different types of solutions into separated chambers of a receiving receptacle.

BACKGROUND OF THE INVENTION

Hyperalimentation therapy is the intravenous feeding of nutrients to patients. A typical solution would include a protein-carbohydrate mixture. It is used primarily to meet the patient's protein and caloric requirements that are unable to be satisfied by oral feeding. The protein may be in the form of free-amino acids or protein hydrolysate and the carbohydrate commonly is dextrose. In addition to the protein and carbohydrate, vitamins (water-soluble and fat-soluble) and electrolytes also can be supplied in this therapy.

Each of these parenteral ingredients and the combination thereof are particularly susceptible to the growth of deleterious organisms and it is desirable that they be administered to the patient in a sterile condition. In addition, the solutions are tailor made to specific patient requirements under the direction of a physician. Thus, because these protein and carbohydrate solutions must be combined close, but prior, to their time of use, their compounding must be performed under sterile conditions to avoid organism growth.

As a part of this compounding, the solutions that are to be administered intravenously are transferred into a total parental nutrition bag (commonly referred to as a TPN bag). Such bags are designed for home use or use in a hospital or care facility. Once filled they can be stored for a limited period of time in a standard refrigerator. The bags are filled with the solutions by a pharmacist either by gravity or by a device known as a high speed bulk compounder. Such compounders typically are capable of supplying solutions from up to nine different source bags (and possibly more) or containers to a receiving product bag at relatively high flow rates.

The source containers may be hung from a framework of the compounder while the receiving bag is hung from a load cell that measures the weight of the receiving bag. A pump set consisting of a number of pump legs (for example, nine or more such legs) or flow paths is designed to be used with the compounder. Each of the pump legs includes flexible tubing and terminates on one end with a piercing administration spike or similar connector that is used to connect the leg of the pump set to one of the source containers. The other end of each leg is coupled to one of the inlet ports of a common manifold equipped with an exit port that is adapted to be coupled to a fill tubing connected to the receiving TPN product bag.

In those instances where a high-speed compounder is used, each leg of the pump set is associated with a different peristaltic pump or pump station of the compounder. A microprocessor in the compounder controls each of the peristaltic pumps or pump stations to thereby control the amount of solution being supplied from each source container through the particular pump leg and the manifold to the receiving product bag. The amount of solution being supplied from each source container is in part determined by information being supplied to the microprocessor of the weight being measured at selected times by the load cell from which the receiving bag is suspended. The peristaltic pumps draw solutions from each of the source containers sequentially under the control of the microprocessor and the solutions flow through the common manifold and the fill tubing into the receiving product bag.

A problem arises when one of the fluids to be introduced into the product bag is a lipid solution. Lipid solutions are essentially fat emulsions and typically are placed into a separate compartment within the product bag which is isolated from the remaining mixture until immediately before (or very soon before) the solution is administered to a patient. This isolation is necessary because the lipid solution, if mixed with the other ingredients ahead of time, clouds the overall solution mixture and renders it unusable. This phenomena is known in the art as "hazing." Because of the undesirability of mixing lipids with the other solutions prior to the time of administration, a problem has existed in the prior art where a residual amount of the lipid solution is allowed to remain in a common volume of the manifold after a lipid solution is pumped through but before the next non-lipid solution is pumped through. When the subsequent solution is pumped through, the residual lipid solution is carried into the product bag and hazing results.

One solution has involved the use of a chambered product bag. By pumping the lipids into a separate chamber of the product bag, the lipids will not mix and "haze" the solution. Immediately before the solution is used, the separated chamber with the lipids is allowed to mix with the remaining solution to form the product solution. To fill the chambered bag using conventional compounders, one line of the compounder must be devoted specifically for lipids and be attached directly to the separated chamber of the product bag. By using the compounder in this manner, however, one line is not used if the overall solution does not require a lipid component.

SUMMARY OF THE INVENTION

The present invention is directed to a tube set for dispensing components into a product bag. The tube set comprises a plurality of tubing lines, a manifold, and a bypass. The manifold has a plurality of inlets, each inlet adapted for connection to a respective tubing line. The manifold also has an outlet connectable to a first feed tube of a product bag. The bypass is associated with at least one of the plurality of tubing lines. The bypass has a bypass inlet connectable to the tubing line associated with the bypass. The bypass also has at least two outlets. A first outlet is connected to a tube line in fluid communication with an inlet of the manifold and a second outlet is removably connectable to a second feed line in fluid communication with the product bag.

According to another embodiment, the present invention is directed to a bypass for a tube set. The tube set includes a manifold and a plurality of tubing lines for dispensing fluid components into a product bag. The bypass comprises an inlet fluid passage adapted for connection to a tubing line of the tube set, an outlet adapted to receive a tubing line in fluid communication with the product bag, and a bypass fluid passage adapted for connection to a tubing line in fluid communication with the manifold. The bypass is configured such that fluid enters the bypass inlet fluid passage and exits through the outlet only when the outlet is connected to a tubing line in direct fluid communication with the product bag.

An exemplary method of the present invention is a method for selectively dispensing fluid components into a product bag attached to a tube set of a bulk compounder. The bulk compounder includes a product bag attached to a tube set having a plurality of tube lines, a manifold, and a bypass having a fluid passage with an inlet and at least two outlets. The method includes providing liquid components to be dispensed into the product bag with one of the liquid components to be maintained separately from the other liquid components, inserting a tube line in fluid communication with the product bag into the bypass first outlet, blocking the bypass second outlet in fluid communication to the manifold, and dispensing the fluid component to be maintained separate from the other liquid components through the bypass and into the product bag, independent of the manifold.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
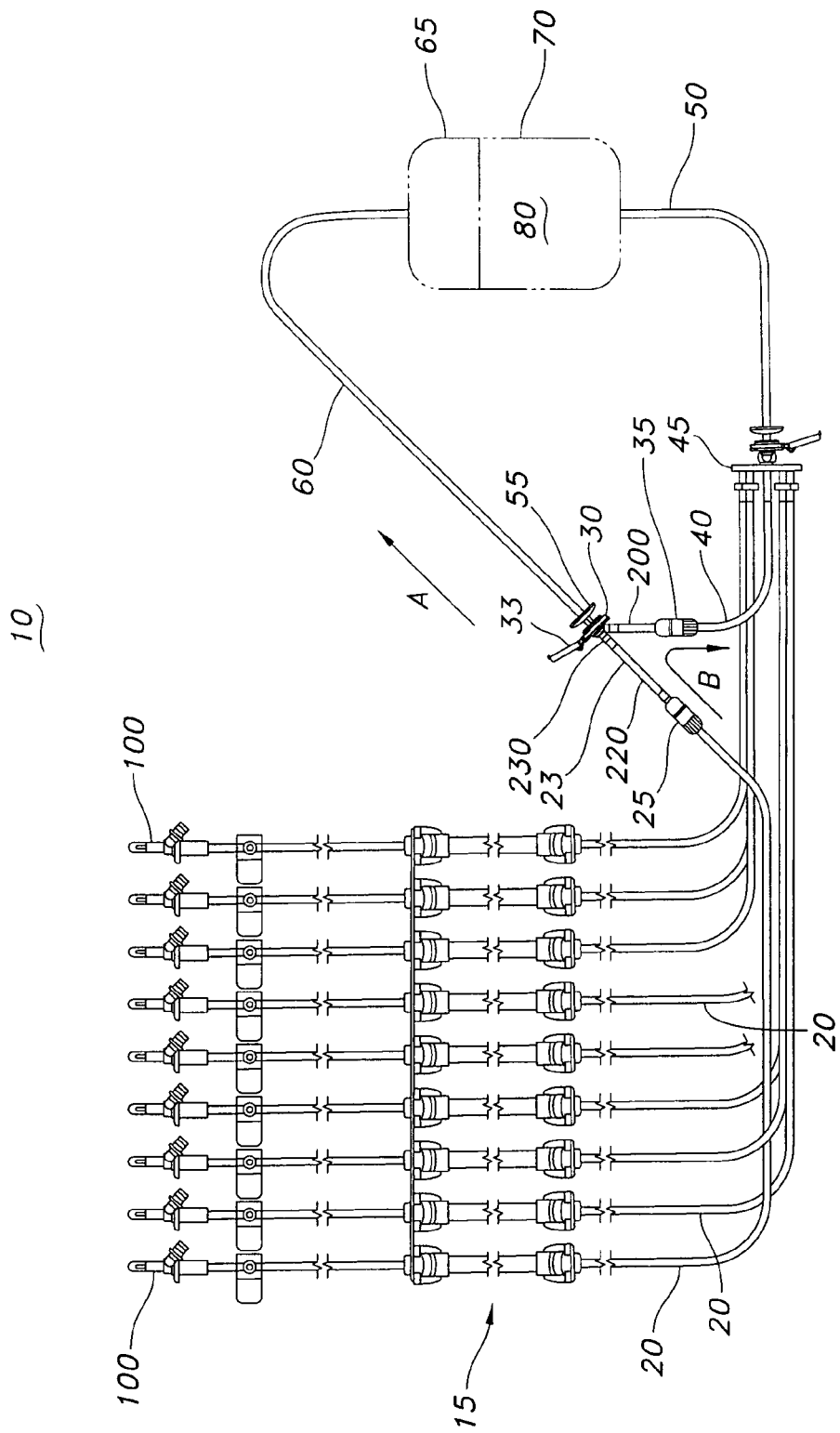
FIG. 1 illustrates an exemplary bulk compouder having a bypass according to an embodiment of the invention.

Referring to the Figures where like numerals represent like features, FIG. 1 shows a pharmaceutical compounding system 10. System 10 can be used for mixing or compounding two or more selected liquids and/or drugs intended to be administered to a human being or an animal. In use, system 10 serves to transfer two or more of individual prescribed liquids and/or drugs from multiple source containers (e.g., individual vials, bottles, syringes, or bags) into a single collecting container (e.g., a bottle, syringe, or bag), so that the mix of liquids and/or drugs can be administered (e.g., intravenously) to an individual in need.

As one example, due to injury, disease, or trauma, a patient may need to receive all or some of his or her nutritional requirements intravenously. In this situation, the patient will typically receive a basic solution containing a mixture of amino acids, dextrose, and fat emulsions, which provide a major portion of the patient's nutritional needs, which is called total parenteral nutrition, or, in shorthand, TPN. In this arrangement, a physician will prescribe a mixture of amino acids, dextrose, and fat emulsions to be administered, as well as the frequency of administration. To maintain a patient for an extended period of time on TPN, smaller volumes of additional additives, such as vitamins, minerals, electrolytes, etc., are also prescribed for inclusion in the mix. Using system 10, under the supervision of a pharmacist, the prescription order is entered and individual doses of the prescribed liquids, drugs, and/or additives are accordingly transferred from separate individual source containers for mixing in a single container for administration to the individual.

There are other environments where system 10 is well suited for use. For example, in the medical field, system 10 can be used to compound liquids and/or drugs in support of chemotherapy, cardioplegia, therapies involving the administration of antibiotics and/or blood products therapies, and in biotechnology processing, including diagnostic solution preparation and solution preparation for cellular and molecular process development. Furthermore, system 10 can be used to compound liquids outside the medical field.

Tube set 15 is a part of system 10. Tube set 15 includes lengths of transfer tubing line 20, which are joined at one end to a common manifold 45. At the opposite ends of the transfer tubing 15 are spikes or releasable couplings 100. Couplings 100 can be inserted in conventional fashion through a diaphragm carried by the associated source solution container (not shown), which allows flow communication between the source solution container and the respective transfer tubing line 20. From manifold 45, a first feed line 50 is coupled to a product bag 80. As shown in the embodiment of FIG. 1, product bag 80 has two compartments, a lower compartment 70 in connection with first line 50, and an upper compartment 65 in connection with a second feed line 60. Transfer tubing lines 20, first feed line 50, and second feed line 60 can be made from flexible, medical grade plastic material, such as polyvinyl chloride plasticized with di-2-ethylhexyl-phthalate. Likewise, product bag 80 can be made from a flexible, medical grade plastic, semi-rigid plastic or glass.

FIG. 1 illustrates system 10 having a bypass 23 for directing liquids through manifold 45 or directly to upper compartment 65 of product bag 80 by way of second feed line 60. As discussed above, once the lipid solutions are mixed with other types of solutions, the shelf life for the mixed solution (i.e., the amount of time before the solution needs to be used) is relatively short. Thus, there is a need to prepare dual-chambered bags having lipid solution dispensed into one compartment of the dual chambered product bag without wasting a tubing line or without the added need for a complete separate transfer tube line.

Figure 2:
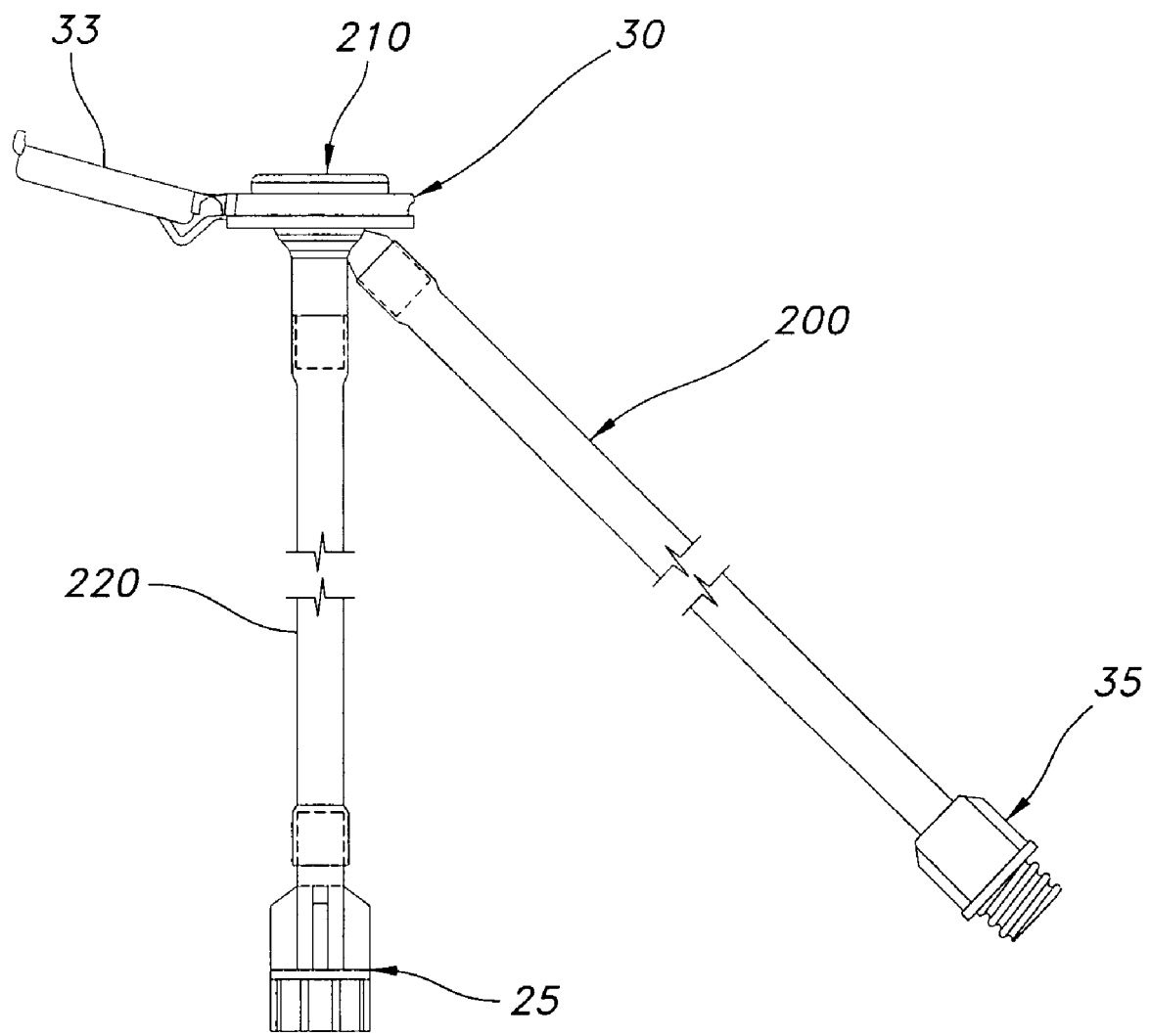
FIG. 2 illustrates an exemplary bypass according to another exemplary embodiment of the present invention.

FIG. 2 illustrates an embodiment of bypass 23 of system 10. Bypass 23 has inlet 25 of inlet fluid passage 220, which can be adapted for fluid communication with transfer tubing line 20 (not shown in FIG. 2). Connected to inlet fluid passage 220 is bypass fluid passage 200 forming a three-way junction at outlet 30. Bypass fluid passage 200 also has outlet 35 for connection with a tubing line (not shown in FIG. 2) to be in fluid communication with manifold 45. Alternatively, bypass 23 can be described as having an inlet connectable to at least one tubing line 20 and two outlets, where one of the outlets is connectable to a tube in fluid communication with an inlet of manifold 45. The second outlet is removably connectable to second feed line 60 of product bag 80.

Also shown in FIG. 2 is flip-top cap 33 which is adapted to cover outlet 30 when second feed line 60 is not connected to outlet 30. Disposed within outlet 30 is a resealable membrane 210 that is self-sealable when punctured, such as a diaphragm valve. Membrane 210 allows a male portion of first feed line 60 to be inserted into outlet 30. Membrane 210 prevents fluids traveling through bypass 23 from escaping. Although membrane 210 is described as a membrane, it can be a washer or other suitable device that would prevent fluid from escaping the connection between second feed line 60 and outlet 30 as would be understood by one skilled in the art.

Figure 3:
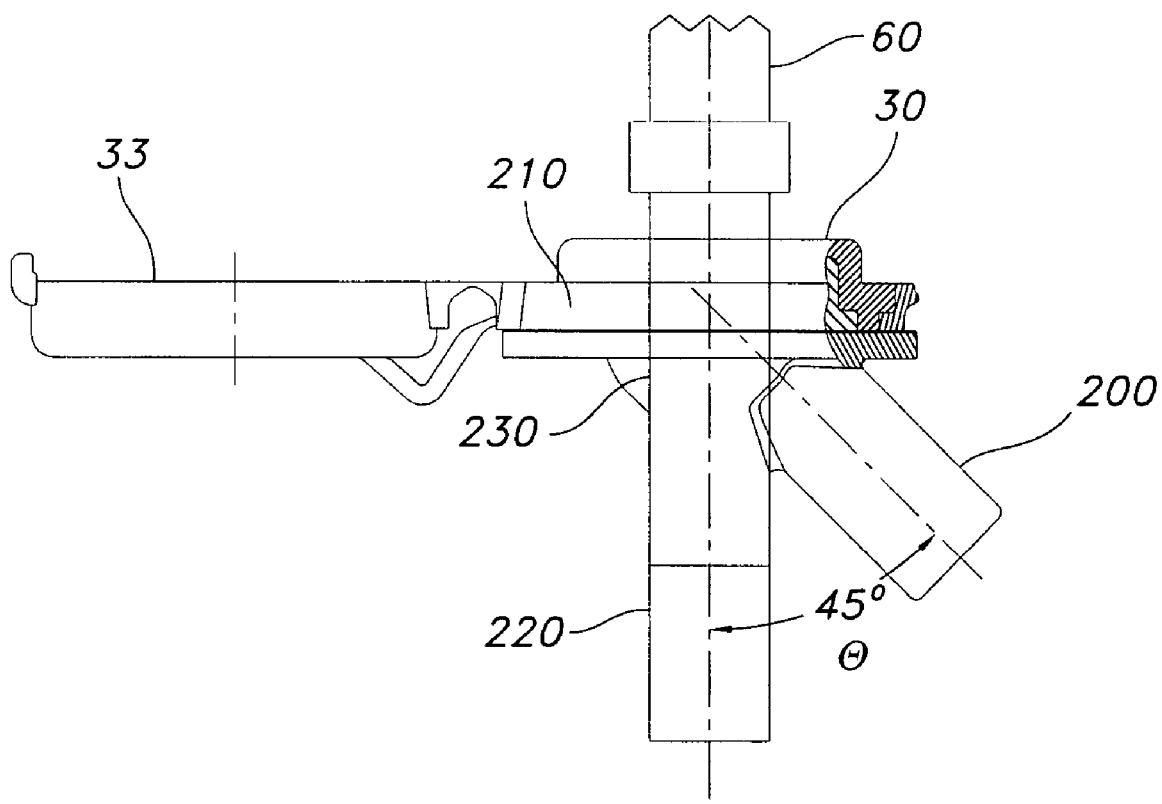
FIG. 3 is an enlarged view of an exemplary bypass according to the present invention.

FIG. 3 is an enlarged and partially cut-away view of inlet fluid passage 220 and bypass fluid passage 200 at outlet 30 with second feed line 60 inserted into outlet 30. According to this embodiment, second feed line 60 has a male connector at the end which meets bypass 23 at bypass outlet 30, which is a female end. In the embodiment shown in FIG. 3, the male end of second feed line 60 is a hollow penetrating probe 230 that pierces membrane 210. As probe 230 is fully inserted into outlet 30, probe 230 seals bypass fluid passage 200 from inlet fluid passage 220. By sealing or blocking bypass fluid passage 200, fluids flow into inlet fluid passage 220 and into second feed line 60. The other end of second feed line 60 is adapted for connection to upper compartment 65 of compartmentalized product bag 80 as shown in FIG. 1. Likewise, when probe 230 of second feed line 60 is removed from outlet 30, resealable membrane 210 closes and fluid flows from inlet fluid passage 220 through to bypass fluid passage 200. Bypass fluid passage 200 is in fluid communication with manifold 45 by way of a bypass to manifold tubing line 40 (shown in FIG. 1).

As shown in the embodiment of FIG. 3, bypass 23 is shaped similar to a "y". Bypass 23 is a three-way connector and may also be shaped like a "T". Between inlet fluid passage 220 and bypass fluid passage 200 is the angle θ. Angle θ can be greater than 0° to less than 180°, preferable less than 90°. According to the embodiment shown in FIG. 3, angle θ is 45°.

Referring again to FIG. 1, fluid components from tube set 15 connected to individual fluid bottles (not shown) through couplings 100, deliver liquids that flow to manifold 45 and through first feed line 50 into product bag 80. When a composition of liquids calls for a component that must be maintained separate until just before use, one tube line 20 from tube set 15 is connected to inlet 25 of bypass 23. A second feed line 60 is connected to outlet 30 of bypass 23. Second feed line 60 is in direct fluid communication with upper compartment 65 of product bag 80. In this configuration, the liquid to be maintained separate will flow through tube line 20 connected to bypass 23 and exit outlet 30 connected to second feed line 60 as shown by line A. In this configuration, the fluid (e.g. a lipid solution) will not pass through manifold 45 and prematurely mix with the other liquid components, but rather will directly flow to upper chamber 65 of product bag 80 independent of manifold 45.

When a lipid solution is not used in the formulation, i.e., when components of the liquid need not remain separate from the other components, second feed line 60 may be removed from bypass 23. Thus, the liquid in the tube line connected to bypass inlet 25 will flow to bypass 23 and will exit via bypass fluid passage 200, which is connected via tubing 40 to manifold 45. The fluid flow direction is shown by line B in FIG. 1. Once the fluid enters manifold 45, it exits manifold 45 by way of first feed line 50, common to the other tubing lines 20, and flows into lower compartment 70 of product bag 80.

According to an embodiment of the present invention, tube set 15 connected to manifold 45 and bypass 23 can be fabricated independently and joined together to form a single device made up of these individual components. Preferably, these components can be ultrasonically welded to their respective mate. The means of joining the components are discussed in detail below. The primary advantage to such a construction is ease of manufacture.

Bypass 23 could be made from any of a number of suitable materials, including plastics, such as polycarbonates, that are suitable to handle the pharmaceutical and food preparations that will be passing therethrough. The suitable materials should also preferably be such that they can be injection molded to form the parts of the device, or the whole device, and one skilled in the art would know such materials.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method for selectively dispensing fluid components into a product bag attached to a tube set of a bulk compounder having at least one tubing line, a manifold, and a bypass having a fluid passage with an inlet, a first outlet in fluid communication with the manifold, and a second outlet in fluid communication with the product bag, the method comprising the steps of:
    providing liquid components to be dispensed into a product bag wherein one of the liquid components is maintained separate from the other liquid components;
    inserting a tubing line in fluid communication with the product bag into the second outlet;
    blocking the first outlet in fluid communication to the manifold; and
    dispensing a fluid component to be maintained separate from the other liquid components through the second outlet and into the product bag, independent of the manifold.

2. The method of claim 1, wherein the step of blocking the first outlet in fluid communication to the manifold comprises inserting a hollow probe end of the tubing line into the fluid passage and past the first outlet such that the probe end obstructs the first outlet and prevents fluid from flowing from the inlet to the first outlet.

3. The method of claim 1, wherein the liquid component to be maintained separate is a lipid solution.

4. The method of claim 1, wherein the step of inserting a tubing line into the second outlet, comprises opening a flow control device of the second outlet.

5. A method for selectively dispensing fluid components into a product bag attached to a tube set of a bulk compounder having at least one tubing line, a manifold, and a bypass having a fluid passage with an inlet and at least two outlets, the method comprising the steps of:
    providing liquid components to be dispensed into a product bag;
    inserting a tubing line in fluid communication with the product bag into the second outlet;
    blocking the first outlet in fluid communication to the manifold; and
    dispensing a fluid component through the second outlet and into the product bag, independent of the manifold.

6. The method of claim 5, wherein the step of blocking the first outlet in fluid communication to the manifold comprises inserting a hollow probe end of the tubing line into the fluid passage and past the first outlet such that the probe end obstructs the first outlet and prevents fluid from flowing from the inlet to the first outlet.

7. The method of claim 5, further comprising the steps of:
    removing the tubing line in fluid communication with the product bag from the second outlet;
    blocking the second outlet;
    unblocking the first outlet in fluid communication to the manifold; and
    dispensing the fluid component through the first outlet and manifold.

8. The method of claim 7, wherein the step of blocking the second outlet comprises sealing a membrane of the second outlet.

9. The method of claim 7, wherein the step of blocking the second outlet comprises covering the second outlet with a flip-top cap.

10. The method of claim 7, wherein the step of unblocking the first outlet is completed by the step of removing the tubing line from the second outlet.

11. A method for selectively dispensing fluid components through a bypass, the bypass having a fluid passage with an inlet, a first outlet in fluid communication with a first bag compartment, and a second outlet that is sealed:

inserting a tubing line into the second outlet to unseal the second outlet;

connecting the tubing line in fluid communication with a second bag compartment that is fluidly separate from the first bag compartment;

sealing the first outlet to prevent flow of fluid to the first bag compartment; and delivering a first fluid component into the inlet of the bypass and through the second outlet to the second bag compartment.

12. The method of claim 11, wherein the step of sealing the first outlet is completed by the step of inserting a tubing line into the second outlet.

13. The method of claim 11 further comprising the steps of:

stopping delivery of the first fluid component into the inlet of the bypass;

removing the tubing line from the second outlet;

sealing the second outlet to prevent flow of fluid to the second bag compartment;

unsealing the first outlet; and delivering a second fluid component into the inlet of the bypass and through the first outlet to the first bag compartment.

14. The method of claim 13, wherein the step of sealing the second outlet is completed by the step of removing the tubing line from the second outlet.

15. The method of claim 13, wherein the steps of sealing the second outlet to prevent flow of fluid to the second bag compartment and unsealing the first outlet are both completed by the step of removing the tubing line from the second outlet.

16. The method of claim 11 wherein the first bag compartment and second bag compartment are located in the same fluid bag.

* * * * *